United States Patent [19]

Palsson

[11] Patent Number: 5,811,274

[45] Date of Patent: Sep. 22, 1998

[54] METHODS, COMPOSITIONS AND APPARATUS FOR CELL TRANSFECTION

[75] Inventor: Bernhard Ø. Palsson, Ann Arbor, Mich.

[73] Assignee: The Regents of the University of Michigan, Ann Arbor, Mich.

[21] Appl. No.: 353,531

[22] Filed: Dec. 9, 1994

[51] Int. Cl.$^6$ .............................. C12N 15/63; C12N 7/01
[52] U.S. Cl. ................................... 435/172.1; 435/235.1; 945/52
[58] Field of Search .............................. 435/172.1, 172.3, 435/252.3, 320.1, 235.1; 935/52, 55

[56] References Cited

U.S. PATENT DOCUMENTS

| | | | |
|---|---|---|---|
| 1,316,789 | 9/1919 | Grimwood et al. | 210/474 |
| 3,839,155 | 10/1974 | McAleer et al. | 435/293.2 |
| 4,159,933 | 7/1979 | Allington et al. | 204/543 |
| 4,164,464 | 8/1979 | Allington et al. | 204/600 |
| 4,201,845 | 5/1980 | Feder et al. | 435/297.2 |
| 4,301,010 | 11/1981 | Eddleman et al. | 210/406 |
| 4,339,537 | 7/1982 | Sogi et al. | 435/240.243 |
| 4,632,761 | 12/1986 | Bowers et al. | 210/650 |
| 5,036,006 | 7/1991 | Sanford et al. | 435/172.1 |
| 5,139,951 | 8/1992 | Butz et al. | 435/297.5 |
| 5,260,211 | 11/1993 | Matsuda et al. | 435/240.24 |
| 5,399,493 | 3/1995 | Emerson et al. | 435/172.3 |

FOREIGN PATENT DOCUMENTS

| | | |
|---|---|---|
| 252 333 | 6/1987 | European Pat. Off. . |
| WO 92/11355 | 9/1992 | European Pat. Off. . |
| 3-151883 | 6/1991 | Japan . |
| 91-234068 | 6/1991 | Japan . |
| 5-328966 | 12/1993 | Japan . |
| 94-021918 | 12/1993 | Japan . |
| WO 93/05815 | 1/1993 | WIPO . |
| WO 93/17090 | 2/1993 | WIPO . |
| WO 93/08270 | 4/1993 | WIPO . |
| WO 94/09145 | 4/1994 | WIPO . |
| WO 95/12392 | 5/1995 | WIPO . |
| WO 95/19427 | 7/1995 | WIPO . |

OTHER PUBLICATIONS

Grass, George M. and Sweetana, Stephanie A. "In Vitro Measurement of Gastrointestinal Tissue Permability Using a New Diffusion Cell." Pharma. Res. 5:372–376 (1988).
The Controlled Environment Incubator Shaker, New Brunswick Scientific Co. Catalog (1966) pp. 1–8.
Kriegler, Michael, *Gene Transfer and Expression*. W. H. Freeman and Company, New York, New York. pp. 1–242 (1990).
Cornetta, Kenneth and Anderson, W. French., "Protamine Sulfate as an Effective Alternative to Polybrene in Retroviral–Mediated Gene–Transfer: Implications for Human Gene Therapy." J. Virol. Methods. 23:187–194 (1989).
Paul, Ralph W. et al., "Increased Viral Titer Through Concentration of Viral Harvests from Retroviral Packaging Lines." Human Gene Ther. 4:609–615 (1993).
Bodine, David M. et al., "Development of a High–Titer Retrovirus Producer Cell Line Capable of Gene Transfer into Rhesus Monkey Hematopoietic Stem Cells." Proc. Natl. Acad. Sci. USA. 87:3738–3742 (1990).
Cassel, Aliza et al., "Retroviral–mediated Gene Transfer into CD34–Enriched Human Peripheral Blood Stem Cells." Exper. Hema. 21:585–591 (1993).
Kaufman, Randal J. "Vectors Used for Expression in Mammalian Cells." Meth. Enzy. 185:487–537 (1990).
Cussler, E.L. *Diffusion, Mass Transfer in Fluid Systems*. Cambridge Iniversity Press, Cambridge. pp. 75–78 (1987).
Palsson, B. *Activation, Metabolism and Perfusion of the Heart*. Sideman, S. and Beyar, R. (Editors) Martinus Nijhoff Publishers. Boston, Mass. 585–620, (1987).
Hidalgo, Ismael J. et al., "Characterization of the Unstirred Water Layer in Caco–2 Cell Monolayers Using a Novel Diffusion Apparatus." Pharma. Res. 8:222–227 (1991).
Mulligan, Richard C., "The Basic Science of Gene Therapy." Science 260:926–932 (1993).
Bluestone, Mimi, "Genes in a Bottle." Bio/Technology 10:132–136 (1992).
Langer, Robert and Vacanti, Joseph P., "Tissue Engineering." Science 260:920–926 (1993).
Verma, Inder M., "Gene Therapy." Sci. Amer. 77–84 (1990).
Krauss, John C., "Hematopoietic Stem Cell Gene Replacement Therapy." Biochimica et Biophysica Acta. 1114:193–207 (1992).
Kotani, Hitoshi et al., "Improved Methods of Retroviral Vector Transduction and Production of Gene Therapy." Human Gene Ther. 5:19–28 (1994).
Lynch, Carmel M. and Miller, A. Dusty, "Production of High–Titer Helper Virus–Free Retroviral Vectors by Cocultivation of Packaging Cells with Different Host Ranges." J. Virol. 65:3887–3890 (1991).
Morgan, Jeffrey R. et al., "Advances in Recombinant Retroviruses for Gene Delivery." Advances. Drug Del. Review. 12:143–158 (1993).
Keown, Wayne A. et al., "Methods for Introducing DNA into Mammalian Cells." Methods in Enzy. 185:527–537 (1990).
Davison, Andrew J. and Elliot, Richard M. *Molecular Virology, A Practical Approach*. IRL Press, New York, New York, Chptr 6, 171–197 (1992).
Bunnell, Bruce A. et al., "High–efficieny Retroviral–Mediated Gene Transfer into Human and Nonhuman Primate Peripheral Blood Lymphocytes." *Proc. Natl. Acad. Sci. USA* 92:7739–7743 (1995).

(List continued on next page.)

*Primary Examiner*—George C. Elliott
*Assistant Examiner*—Robert Schwartzman
*Attorney, Agent, or Firm*—Campbell & Flores LLP

[57] ABSTRACT

This invention provides methods, compositions and apparatus for increasing the transfection efficiency of target cells by particles, especially retroviral particles, compared with that achieved by current methods. The transfection method comprises depositing the particles on a cell growth support and contacting target cells with the particle-loaded cell growth support.

41 Claims, 6 Drawing Sheets

OTHER PUBLICATIONS

Russell, Stephen J. et al., "Retroviral Vectors Displaying Functional Antibody Fragments." *Nucleic Acids Res.* 21:1081–1085 (1993).

Kompier, R. et al., "Use of a Stationary Bed Reactor and Serum–free Medium for the Production of Recombinant Proteins in Insect Cells." *Enzyme Microb. Technol.* 13:822–827 (1991).

Dunny, Gary M. et al., "Improved Electroporation and Cloning Vector System for Gram–Positive Bacteria." App. Envirn. Micro. 57:1194–1201 (1991).

Gaertig, Jacek and Gorovsky, Martin A. "Efficient Mass Transformation of Tetrahymena Thermophila by Electroporation of Conjugants." Proc. Natl. Acad. Sci. USA. 89:9196–9200 (1992).

Russel et al. (1993) Retroviral vectors displaying functional antibody fragments. Nucleic Acids Res. 21:1081–1085 (1993).

Mulligan (1993) The basic science of gene therapy. Science 260:926–932 (May 1993).

Langer et al. (1993) Tissue engineering. Science 260:920–926, (May 1993).

FIG. 1

METHODS, COMPOSITIONS AND APPARATUS FOR CELL TRANSFECTION

BACKGROUND OF THE INVENTION

This invention relates generally to genetic engineering, and more specifically, to methods of increasing transfection efficiency of target cells.

Genetic engineering technology is used routinely to transfect cells. Transfection is the introduction of a foreign gene(s) into a target cell and the incorporation of that gene into a chromosome of the target cell. Once inside the target cell, a functional foreign gene can produce the RNA and protein product it encodes. Transfection has diverse applications in fermentation, research, agriculture, pharmaceuticals and medicine.

A particularly important application of transfection is gene therapy. Gene therapy has the potential to permanently treat diseases and deliver new therapeutic proteins and RNA that currently cannot be used. In gene therapy, a patient receives a functional foreign gene which produces a product that affects the disease or condition. Since the foreign gene can be stably incorporated into the patient's genome, the foreign gene has the potential to produce the product for the life of the patient. The patient receives the foreign gene by transfecting target cells ex vivo and administering the transfected cells to the patient or the foreign gene can be directly administered to the patient and the cells transfected in vivo.

A requirement of all transfection methods is that the foreign gene gets into the target cell. Many transfection methods have been developed but all can be classified as either direct or indirect methods. In direct methods, a genetic engineer injects the foreign gene into individual target cells using a microcapillary or microprojectile. Indirect methods involve the target cells passively or actively taking up the foreign gene. Indirect methods are diverse and include, for example, pinocytotic uptake of DNA-calcium phosphate and fusion of liposomes with the plasma membrane of the target cell. A very effective method is to use viral particles to infect the target cell because, once inside the target cell, foreign genes often express themselves at consistently higher levels by this method than by other methods.

Viral particles are themselves quite diverse and include DNA viruses, such as SV40, polyoma, adenovirus, Epstein-Barr, vaccinia, herpes simplex and baculovirus, and RNA viruses, such as tobacco mosaic virus, cucumber mosaic virus, brome mosaic virus and retrovirus. Retroviruses are particularly useful viral particles because, once inside the target cell, these viruses lead to stable transfections. Retroviruses which are replication-incompetent appear well suited for gene therapy because, in principle, these viruses do not produce any wild-type virus and cannot infect other cells after infecting the target cell. Replication-incompetent viruses are produced in so called "packaging cells" because these cells "package" the foreign gene into viral particles which can infect, but not replicate.

The major problem with indirect transfection methods is that they are inefficient at transfecting target cells. Transfection efficiencies of 1–20% are achieved but, for human target cells, the transfection efficiency is at the lower end of the range. The transfection efficiency is the number of target cells containing at least one copy of the foreign gene divided by the total number of target cells. Thus, most current indirect transfection methods waste large amounts of costly target cells, carriers and foreign genes because only a small fraction of exposed target cells is transfected. This inefficient method particularly limits development of gene therapy because gene therapy requires many transfected target cells. In certain circumstances, higher transfection efficiencies are possible but often heroic measures are needed to achieve them. For example, bone marrow target cells can be cultured for several weeks with repeated exposures to retroviral particles. Such methods are not practical because of expense, complexity or incompatibility of the target cells and particles. There is a need for a more efficient, easy-to-use, generally applicable transfection method.

Contact between target cells and viral particles is essential for transfection to occur. Generally, indirect viral transfection occurs by culturing target cells with viral particles suspended in the cell culture medium. All indirect transfection methods are based on random contact between viral particles and target cells. Typically, the culture is gently agitated during transfection and suspended viral particles contact target cells by chance. Although specific target cells can be selected for transfection using various techniques, the contact between target cells and viral particles in these methods remains a random event. Methods for selectively transfecting target cells include bridging antibodies between viral and target cell antigens and chemically modifying particles for specific target cell receptors. Current indirect transfection methods are therefore limited to random contact between viral particles and target cells.

Increasing the concentration of viral particles increases contact between viral particles and target cells. However, the viral particle concentration that can be used for transfection is limited because the proportion of infectious viral particles decrease as the viral particles are concentrated. Various methods are used to concentrate retroviral particles including polyethylene glycol precipitation, sucrose gradient centrifugation, pelleting by centrifugation, aqueous two-phase systems, ammonium sulfate precipitation, and hollow fiber ultrafiltration. A measure of viral particle concentration is titer that, for replication-incompetent retrovirus, is typically about $10^4$ to $10^5$ colony forming units (CFU)/ml. Viral particle concentration limits the transfection efficiency of current viral transfection methods by limiting the contact between viral particles and target cells.

Current indirect transfection methods require chemical additives to transfect target cells. Chemical additives allow viral particles to enter target cells more easily. Chemical additives include, for example, polybrene and protamine sulfate. In current methods, chemical additives are required because particle-target cell contact is so infrequent it is necessary to maximize the number of particles that enter target cells once contact occurs. Without chemical additives, even the relatively low transfection efficiencies achieved by current methods would not be possible. Chemical additives are undesirable for gene therapy because the chemical additives pose a contamination concern.

Another problem with current methods is that some target cells cannot be transfected because the particles cannot contact the target cells in culture. For example, hematopoietic stem cells (HSCs), a prime target for gene therapy applications, are often grown in cell culture in association with accessory cells (stromal cells). The HSCS position themselves between stromal cells and the cell growth support, and become physically inaccessible to retroviruses in the cell culture medium. HSCs cannot be transfected by retroviruses because the stromal cells block retroviral access to the HSC. A method is needed which allows particles to contact target cells even though the target cells are covered over by accessory cells.

Besides contact limitations, low transfection efficiencies can result from cell culture inhibitors that limit target cell growth. Retroviruses require dividing target cells to transfect. Packaging cell culture supernatant contains growth inhibitors that reduce target cell growth. Since the target cells must divide for transfection to occur, inhibitors reducing target cell growth reduce transfection efficiencies. Using current methods, it is difficult to remove inhibitors in the packaging cell culture supernatant from the replication-incompetent retroviruses.

Clearly, there is a need for new transfection methods that improve the efficiency of target cell transfection. New transfection methods are needed which increase particle-target cell contact without adversely effecting particle infectivity and do not require chemical additives to transfect target cells. Further, new transfection methods are needed to transfect target cells that are not normally accessible in culture and to remove growth inhibitors from transfecting cultures. These needs are particularly acute in the field of gene therapy. The present invention satisfies these needs and provides related advantages as well.

SUMMARY OF THE INVENTION

This invention provides a method of transfecting target cells by particles comprising depositing the particles on a cell growth support and contacting the target cells with the particle-loaded cell growth support. In one embodiment of the method, the particles are retroviral particles. Another embodiment further comprises cryopreserving or lyophilizing the particle-loaded cell growth support prior to contacting target cells.

The invention also provides a composition comprising particles capable of transfecting target cells localized on a filter, membrane filter, cell culture surface or tissue engineering material in an amount effective for increasing the transfection efficiency of target cells compared with that achieved by particles suspended in liquid. In one embodiment, the particles are retroviral particles. Another embodiment is a frozen and/or lyophilized particle-loaded cell growth support in which the particles are in an amount effective for increasing the transfection efficiency of target cells compared with that achieved by particles suspended in liquid after freezing and/or lyophilizing.

The invention also provides an apparatus comprising particles contained in a liquid, a cell growth support and means for moving the liquid toward the cell growth support. In one embodiment, the means for moving the liquid comprises a container having a porous cell growth support allowing passage of the liquid through it. Another embodiment is where the means for moving the liquid comprises a container having a solid cell growth support allowing liquid to pass over it. Still another embodiment comprises target cells contained in a liquid, a particle-loaded cell growth support and a means for causing the target cells to move toward the particle-loaded cell growth support.

BRIEF DESCRIPTION OF THE DRAWINGS

Figure 1:
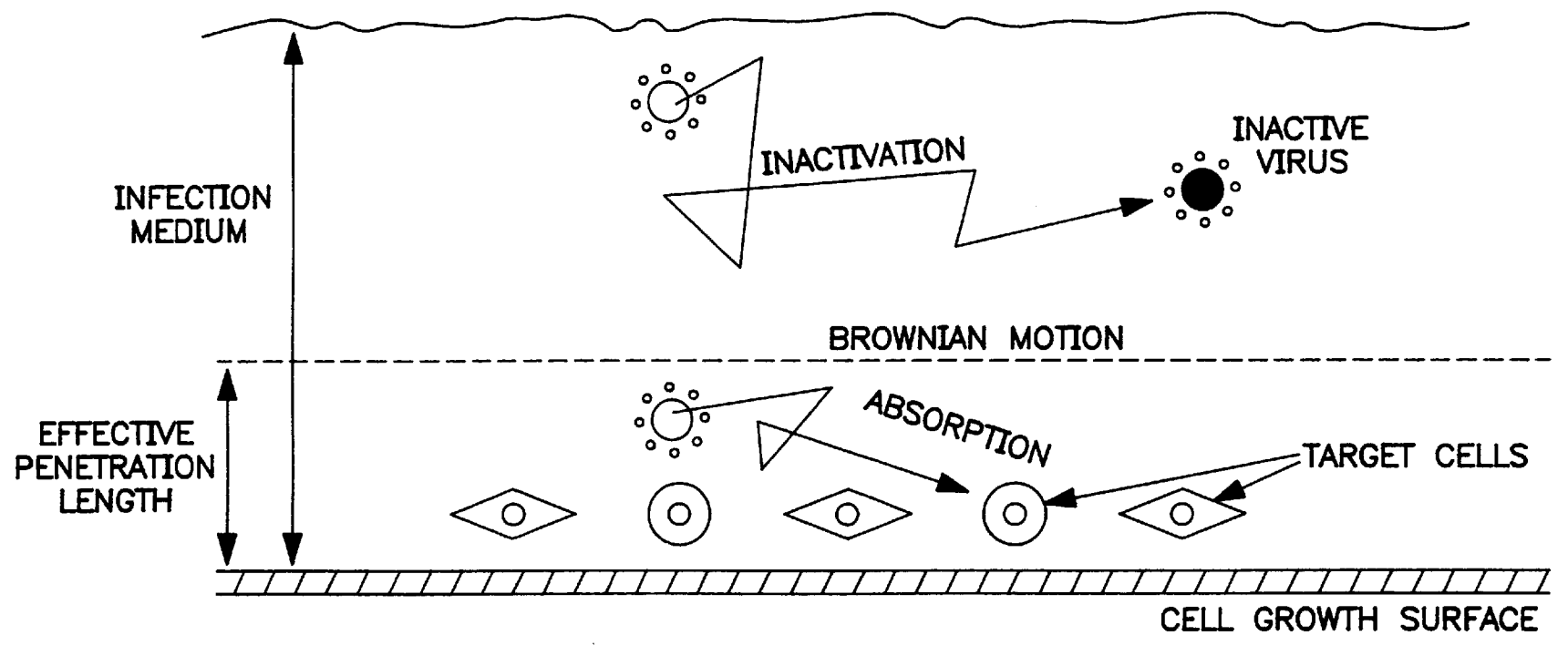

FIG. 1 is a schematic representation of particles undergoing Brownian motion, inactivation and cellular absorption.

DETAILED DESCRIPTION OF THE INVENTION

Figure 2A:
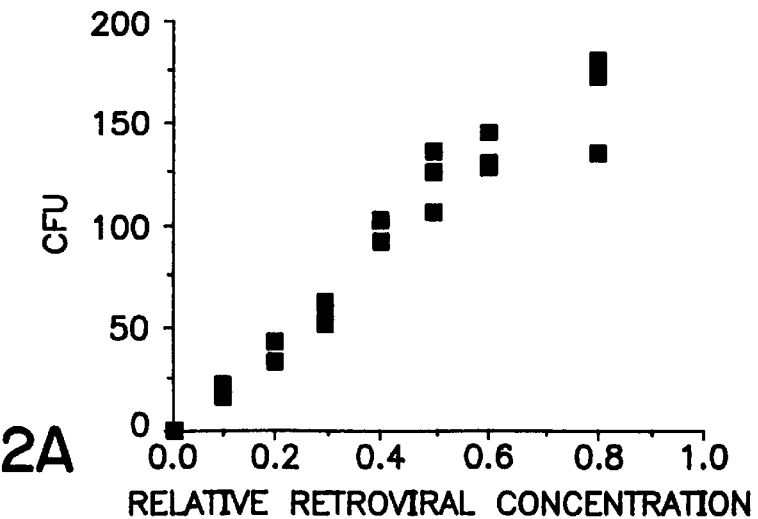
FIGS. 2A–C shows the number of colony forming units (CFU) as a function of (A) retroviral concentration, (B) initial density of target cells, and (c) depth of the liquid layer above the target cells.

The invention provides a new method that dramatically increases the transfection efficiency by increasing the contact between particles and target cells. The contact is increased by localizing particles on a cell growth support and directing target cells to contact the particle-loaded cell growth support. As broadly claimed, the method comprises two steps. First, the particles are deposited on the cell growth support by various means such as filtration or absorption. Second, the target cells are directed to the particle-loaded cell growth support by various means such as gravity sedimentation or filtration. Localizing the particles on the cell growth support increases the contact between particles and target cells, which increases the transfection efficiency compared with that achieved by particles in suspension. Moreover, this method retains the infectivity of viral particles.

The method has broad application as any transfection particle can be used. As used herein, the term "particle" means the combination of any carrier and any foreign gene(s) used to transfect target cells. Carriers include, for example, viruses, liposomes, spheroplasts, red blood cell ghosts, colloidal metals, calcium phosphate, DEAE Dextran and plasmids. Viral carriers include DNA viruses, such as SV40, polyoma, adenovirus, Epstein-Barr, vaccinia, herpes simplex, papilloma particles and baculovirus, and RNA viruses, such as tobacco mosaic virus, cucumber mosaic virus, brome mosaic virus and retrovirus. An embodiment of the retrovirus is a replication-incompetent retrovirus including, for example, replication-incompetent retroviruses produced by packaging cell lines ψ2, ψAM, PA12, PA317, PG13, Clone 32, GP+E-86, ψCRIP, ψCRE, D17-C3, DSN, DAN, PHF-G, Isolde, Q2bn/Q4dh. As used herein "viral particle" means a particle containing a viral carrier and any foreign gene.

Any foreign gene includes any gene(s) wanted for transfection and auxiliary nucleic acid sequences. The foreign gene and/or auxiliary nucleic acid sequences can be either DNA and/or RNA. Auxiliary nucleic acid sequences are any nucleic acid sequences necessary or which improve transfection, expression and/or detection of the foreign gene. Auxiliary nucleic acid sequences include, for example, expression elements, promoters, enhancers and homologous recombination sequences.

Particles are assembled using any method appropriate for the carrier and foreign gene. Diverse methods of assembly are known including, for example, simple precipitation of the foreign gene as DNA with calcium phosphates encapsulation of the foreign gene within liposomes, adsorption of the foreign gene on colloidal metal particles or genetically engineering the foreign gene into the genome of viruses.

Commonly used particles suitable for this method and their methods of assembly are described in many genetic engineering articles including, for example, Kaufman, R. J. "Vectors Used for Expression in Mammalian Cells" in *methods in Enzymology, Gene Expression Technology* Ed by D. V. Goeddel, Pub. by Academic Press, Inc., San Diego, 185:487–511 (1990), Keown, W. A. et al., "Methods for Introducing DNA into Mammalian Cells," in *Methods in Enzymology, Gene Expression Technology* Ed by D. V. Goeddel, Pub. by Academic Press, Inc., San Diego, 185:527–537 (1990), Kriegler, M. *Gene Transfer and Expression A Laboratory Manual*, Pub. by W. H. Freeman and Company, New York, pp 3–81 (1990), Davision, A. J. and Elliott, R. M. *Molecular Virology, A Practical Approach*, IRL Press at Oxford University Press, Oxford, (1993) pp 171–198.

The method has broad application also because any target cell can be used. As used herein, the term "target cell" refers to cells that can be infected by a particle and contact the particle-loaded cell growth support. Target cells include procaryotic and eukaryotic cells. Eukaryotic cells include plant, insect and animal cells. An embodiment are cells useful for gene therapy, either for human or animal use, and include, for example, bone marrow cells, lymphocytes, fibroblasts, keratinocytes, hepatocytes, endothelial cells, neurons, muscle cells, and epithelial cells. Preferred human gene therapy target cells include HSCs. Examples of target cells and their use in gene therapy are discussed in several articles including, for example, Mulligan, R. C. "The Basic Science of Gene Therapy" *Science* 260:926–932 (14 May 1993), Bluestone, Mimi, "Genes in a Bottle," *Bio/Technology* 10:132–136 (February 1992), Krauss, J. C. "Hematopoietic stem cell gene replacement therapy," *Biochimica et Biophysica Acta.* 1114:193–207 (1992), and Verma, Inder, M. "Gene Therapy" *Scientific American* 84:68–74 (1990). One can readily employ other particles and target cells not named but known to the art.

As used herein, the term "cell growth support" means any sterile material on which particles can be deposited ex vivo and is compatible with subsequent ex vivo and/or in vivo transfection of target cells. An embodiment of the cell growth support is disposable. Examples of cell growth supports include filters, membrane filters, cell culture surfaces, and tissue engineering materials. A filter is any porous material capable of collecting particles in suspension and supporting target cells. An embodiment of the filter is that at the bottom surface of a cell culture cup such as COSTAR TRANSWELL insert, FALCON CLYCLOPORE, cell culture insert, NUNC ANOPORE and polycarbonate TC inserts, or MILLIPORE MILLICELL insert. Filters can be made of any material compatible with target cell transfection, including for example, polyethylene terephthalate, polystyrene or polycarbonate. Filters also can be coated with any material compatible with target cell transfection including for example, collagen or polycation. Polycations include, for example, polybrene, protamine or polylysine. Filters can be treated in any manner compatible with target cell transfection including, for example, plasma discharge. Any filter with a pore size capable of supporting target cells can be used, especially a pore size of approximately 0.1 $\mu$m to about 2.0 $\mu$m diameter. A membrane filter is a thin filter made of synthetic or natural materials. An embodiment of the membrane filter is made of nitrocellulose or other cellulose esters. An embodiment of the membrane filter is dialysis membrane made of either synthetic or naturally derived materials such as intestinal segments. See, for example, Grass, G. M. and S. A. Sweetana, "In Vitro Measurement of Gastrointestinal Tissue Permeability Using a New Diffusion Cell" *Pharmaceutical Research* 5(6):372–376 (1988). A cell culture surface is a solid surface to which particles can be localized and on which target cells grown. An embodiment of the cell culture surface is made of glass or plastic which may or may not be coated or treated as above. An embodiment of the plastic cell culture surface includes those dishes, plates, flasks, bottles and hollow-fiber cell culture systems produced by various manufacturers for growing cells including COSTAR, NUNC and FALCON. Tissue engineering materials are materials designed to replace or create new tissues, products or functions in an animal. Tissue engineering materials are diverse and include synthetic materials, natural materials and combinations of both. Tissue engineering materials can be porous or solid and can be designed to remain permanently or temporarily in an animal after implantation. Examples of tissue engineering materials include hollow fibers, synthetic polymer scaffolds, microcapsules, sheaths, rods, discs, dispersions and feeder layers. Applications using tissue engineering materials include, for example, hip replacements, organ transplantations and skin replacement in burns. One application of tissue engineering materials is to provide a substrate on which to grow cells ex vivo to replace damaged or missing tissue in the animal. See, for example, Langer, R. and J. P. Vacanti, "Tissue Engineering" *Science* 260:920–926 (14 May 1993).

The first step of this method is to deposit particles on the cell growth support. Particles can be deposited by any means which localizes particles to the cell growth support and preserves the ability of the particles to transfect target cells. Examples of deposition methods include, but are not limited to, adsorption, absorption, non-covalent chemical bonding, centrifugation, aerosol dispersion, electrophoresis or combinations thereof. Adsorption collects particles on the surface of a cell growth support from fluid containing the particles. An example of adsorption deposition is filtration adsorption which is the collection of particles on a filter or membrane filter as fluid containing the particles flows through the filter or membrane filter. Adsorption from a stagnant liquid or liquid agitated by laminar lateral or circular fluid motion is specifically excluded. Non-covalent chemical bond deposition collects particles by binding particles to chemical binders attached to the cell growth support. The chemical binders include, for example, polycations, antibodies, and adhesion molecules and may or may not be covalently attached to the cell growth support. Polycations include, for example, polybrene, protamine sulfate, and polylysine. Antibodies include, for example, antibodies or fragments thereof which bind retrovirus antigens, especially the eny antigen. Adhesion molecules include, for example, collagen and fibronectin polypeptides or derivatives thereof. Centrifugation collects particles by accelerating particles through the liquid and onto a cell growth support. An example of centrifugation deposition is spinning at sufficient speed a container containing a solid cell growth support and liquid containing particles such that the particles collect on the solid cell growth support. Aerosol dispersion collects particles by applying very small micro-liquid droplets containing particles onto a cell growth support. An example of an aerosol dispersion deposition is a pressurized system including an aerosol jet that sprays particles on a cell growth support. Electrophoresis collects particles by electro-plating particles onto a cell growth support. A particle-loaded cell growth support is cell growth support on which particles have been deposited.

Particles are deposited on the cell growth support in an amount effective for increasing the transfection efficiency of target cells relative to that achieved by particles in suspension. The "amount effective" is a particle density greater than that resulting from particle adsorption due to Brownian motion. In preferred embodiments, the amount effective for the claimed invention is a particle density approximately 2, 5, 10, 100, or 1000 fold greater than that resulting from adsorption due to Brownian motion. An estimate of the maximum particle density due to Brownian motion of approximately $1.6 \times 10^5$ to $1.6 \times 10^6$ particles per $cm^2$ can be calculated for particles having a short half-life. The calculations assume particles with an initial concentration of $10^7$ or $10^8$ particles per cubic centimeter (cc), a diffusion coefficient of $4.5 \times 10^{-8}$ $cm^2$ per sec and a half-life of 5 hours. The calculation boundary conditions are that the initial concentration is the concentration at time zero, there is an exponential decay of virus in the suspension and complete and instantaneous adsorption of the particles occurs at the surface. The calculated estimate is a maximum density whereas the actual density may be less. To achieve a particle density greater than that due to Brownian motion, the liquid flow rate towards the cell growth support must result in a Peclet number greater than unity. The calculations are based on established methods, for example, R. S. Bird, W. E. Steward and E. N. Lightfoot, *Transport Phenomena*, Wiley & Sons (1960). For the definition of Peclet number see, for example, B. O. Palsson in *Activation, Metabolism and Perfusion of the Heart*, S. Sideman and R. Beyar, Eds., Marinue Nijhoff Pub., pp. 594–596 (1987).

"Localized" as used herein means the particles are in physical contact with the cell growth support and accessible to target cells. The number of particles on a cell growth support can be assayed by standard methods currently used to assay viral titers including, for example, radioactivity assays and electron microscopy particle counting assays and/or calculated based on diffusion or mass transport theory. Transfection efficiency can be assayed using standard CPU assays. Optimizing these parameters is routine work not requiring undue experimentation. Comparisons between particles on the cell growth support and in suspension are made using the equivalent conditions, for example, the same target cell concentration or density, age of target, temperature and transfection time.

In the second step of the method, target cells contact the particle-loaded cell growth support. For ex vivo transfection, target cells are "directed" to contact the particle-loaded cell growth support. Any means of directing target cells to the particle-loaded growth support can be used while transfection can occur. For example, target cells can direct themselves to the particles by naturally attaching to a cell growth support. In another embodiment, the target cells are directed gravitationally or centrifugally onto the particle-loaded cell growth support. In another embodiment, the target cells are directed by filtering target cells onto the particle-loaded porous cell growth support as fluid containing the target cells flows through the porous cell growth support.

Although standard transfection culture conditions are generally used, a significant advantage of the present invention is that chemical additives are not required for transfection. Until now, indirect transfection methods required chemical additives for transfection. Chemical additives, such as polybrene and protamine sulfate, increase the proportion of particles entering target cells after particle-target cell contact. Chemical additives, however, are not always desirable and, for gene therapy, pose a contamination concern. In contrast, the broadly-claimed invention does not require chemical additives because excellent transfection efficiency results without them. The broadly claimed method results in frequent _ particle-target cell contact that eliminates the need for maximal particle entry into target cells after contact. The frequent particle-target cell contact of the claimed invention compensates for the infrequent entry of particles into target cells that occurs without chemical additives. Thus, the current transfection method offers, for the first time, the option of transfecting target cells without chemical additives. Other standard transfection culture conditions, such as culture media, temperature and accessory cells, used to transfect target cells by particles in suspension are also used in the method of particles deposited on a cell growth support. See, for example, Cassel, A. et al, "Retroviral-mediated gene transfer into CD34-enriched human peripheral blood stem cells" *Experimental Hematology* 21:585–591 (1993), Kaufman, R. J. "Vectors Used for Expression in Mammalian Cells" in *Methods in Enzymology, Gene Expression Technology* Ed by D. V. Goeddel, Pub. by Academic Press, Inc., San Diego, 185:487–511 (1990), Keown, W. A. et al., "Methods for Introducing DNA into Mammalian Cells," in *Methods Enzymology, Gene Expression Technology* Ed by D. V. Goeddel, Pub. by Academic Press, Inc., San Diego, 185:527–537 (1990), Kriegler, M. *Gene Transfer and Expression A Laboratory Manual*, Pub. by W. H. Freeman and Company, New York, pp 3–81 (1990), Davision, A. J. and Elliott, R. M. *Molecular Virology, A Practical Approach*, IRL Press at Oxford University Press, Oxford, (1993) pp 171–198.

The term "liquid" as used herein is any free flowing, nongaseous or non-solid material compatible with particles and/or transfection of target cells. Different liquids can be used at different stages of the transfection method. For example, the liquid used for depositing particles need not be the same as the liquid used during transfection. Liquids include, for example, buffered and osmotically controlled solutions, any cell culture medium, and supernatant from packaging cells. As discussed above, the liquid may include a chemical additive for improving transfection such as a polycation. Examples of polycations include, polybrene, or protamine sulfate, present at approximately 4 to 10 $\mu$g/ml. See, for example, Cornetta, K and W. F. Anderson, "Protamine sulfate as an effective alternative to polybrene in retroviral-mediated gene- transfer: implications for human gene therapy," *J. Virological Methods*, 23:187–194 (1984).

Inhibitors in the supernatant containing the particles can be removed before the target cells contact the particles. This capability offers significant advantages for replication-incompetent retrovirus transfection. Specifically, growth inhibitors present in the supernatant from packaging cells can be removed before the target cells contact the replication-incompetent retrovirus. Some retroviral packaging cell supernatants inhibit the growth of certain target cell types. For example, commonly-used packaging cell line supernatants, such as from PA317, $\psi$CRIP, and PG13, inhibit growth of primary human cell lines. Target cell growth is required for retroviral transfection and, therefore, removing growth inhibitors increases target cell growth and transfection efficiency. Inhibitors are removed by depositing the particles on the cell growth support, removing the supernatant and replacing the supernatant with a liquid which does not contain the inhibitor and which is compatible with transfection. Methods of removing inhibitors include, for example, adsorbing or absorbing the particles onto the cell growth support and washing the particle-loaded cell growth support with a liquid not containing the inhibitors. See, for example, Paul, R. W. et al. "Increased viral titer through concentration of viral harvests from retroviral packaging lines," *Human Gene Therapy*, 4:609–615 (1993).

Localizing particles on cell growth supports allows transfection of target cells that would be difficult or impossible to transfect by current methods. Many target cells require co-cultivation with accessory cells in order for the target cells to grow. For some target cell types, target cells must grow between the cell growth support and the accessory cells and the particles cannot contact the target cells because accessory cells block access to the target cells. However, a particle-loaded cell growth support contacts the target cell because the target cell is growing on the cell growth support. An example of target cells having this property is the HSCs. HSCs can be more efficiently transfected by particle-loaded cell growth supports than by particles suspended in liquid because the target cells contact the cell growth support.

After ex vivo transfection, the target cells can be used in the culture or removed from the culture. Various standard sterile techniques can be used to remove target cells from the culture including, for example, trypsin digestion to release attached target cells, agitation and aspiration of media containing transfected cells and gravitationally or centrifugally removing the target cells from the cell growth support. An example of a method for removing transfected cells from the culture is to wash the culture with phosphate buffered saline, add trypsin and EDTA, incubate, suspend and remove target cells, inactivate trypsin and resuspend target cells in growth medium. Cells transfected by this method can be used for any purpose including use in fermentation, research, agriculture, pharmaceuticals and medicine. For gene therapy, an embodiment of the application is to administer the transfected target cells to a patient to treat a disease or condition.

The in vivo transfection of target cells is achieved by implanting a particle-loaded tissue engineering material into an animal. The physical contact of the particle-loaded tissue engineering material with the body tissue places the particles in contact with the target cells. Selecting the site of implantation directs the particles to specific tissues or organs. In one embodiment, target cells attach to the particle-loaded tissue engineering material ex vivo and the assembly of target cells, particles, and tissue engineering material is implanted into an animal. In another embodiment the tissue engineering material with attached particles is implanted directly into an animal to transfect target cells in vivo.

See, for example, Langer, R. and J. P. Vacanti, "Tissue Engineering" *Science* 260:920–926 (14 May 1993), especially page 924, third column, third full paragraph and page 925, first column, first full paragraph and Mulligan, R. C., "The Basic Science of Gene Therapy," *Science* 260:926–932 (14 May 1993), especially page 931, first column, first full paragraph.

The particle-loaded cell growth support can be cryopreserved for later use. A particle-loaded cell growth support is cryopreserved using standard methods which preserve the ability of the particles to transfect target cells. Standard cryopreservation methods used for viral particles in suspension can be used, for example, freezing at −1° C./min. and storing the frozen particle-loaded support at −70° C. or colder. An embodiment is to add a cryoprotectant to the particle-loaded cell growth support before freezing, such as glucose, sorbitol or gelatin. Just before use, a frozen particle-loaded cell growth support is thawed using standard methods used for thawing viral particles, for example, rapidly thawing at 37° C. Infectivity is always reduced because of the freezing and thawing process. Cryopreservation and thawing is generally adequate if transfection is retained after freeze/thaw. In comparing transfection efficiencies from cryopreserved particles attached to cell growth supports and suspended in liquid, substantially the same freezing, storage and thawing conditions must be used for both. In an embodiment, frozen particle-loaded cell growth supports are envisioned for commercial sale. See, for example, Elliott, R. M. *Molecular Virology, A Practical Approach*, IRL Press at Oxford University Press, Oxford, (1993) pp 171–198.

The particle-loaded cell growth support can also be dehydrated and preserved dry for later transfection use. A particle-loaded cell growth support is dried using any method that preserves the ability of the particles to transfect target cells. Drying methods include, for example, lyophilizing or air drying. Lyophilizing can be achieved by adding cryoprotectants, quickly freezing, freeze-drying and storing the particle-loaded cell growth support. Cryoprotectants include, for example, glucose, sorbitol and gelatin. Rapid freezing can be achieved, for example, in a dry-ice acetone bath. Lyophilization can be achieved in standard freeze-drying apparatus such as, for example, a MODEL FREEZEMOBIL LYOPHILIZER. Lyophilized material can be stored at low temperature, 4° C. or colder, prior to rehydration and transfection.

Furthermore, apparatuses that allow easy-to-use particle deposition on cell growth supports are developed. The apparatus comprises particles in a liquid, a container which has a cell growth support and means for causing the liquid to move through or over the cell growth support. In one embodiment, the liquid flows through a container having a porous cell growth support, for example, filters having pore sizes ranging from about 0.1 μm to about 2.0 μm, to which the particles attach. The means for moving the fluid through the cell growth support include gravitational, centrifugal, vacuum and pumping means. In an embodiment, particles in the fluid are produced by a separate particle-producing container which is operationally connected to the container which has the cell growth support. The particle-producing container can contain a cell culture that produces particles, such as a viral particle producing cell line. Specifically, such cell cultures could be done in suspension, on suspended microcarriers or on solid surfaces. In an embodiment, the container that has the cell growth support has a porous filter or membrane filter and the fluid flows from the particle-producing container to and through the container which has the filter or membrane filter cell growth support. In one example, the means for liquid flow is a liquid-absorbing matrix, contacting one side of the porous cell growth support, which pulls the fluid through the filter or membrane filter by capillary action. A liquid-absorbing matrix is any sterile material that can draw liquid through the porous cell growth support. Examples of liquid-absorbing material include sponges, cloth, and paper. In another example, the means for liquid flow is any means that applies a partial vacuum to one side of the porous filter or membrane filter. A means for applying a partial vacuum includes any method that can produce a vacuum, for example, an aspirator, roughing pump, peristaltic pump or combinations thereof. In another embodiment, the particles contained in the fluid are recycled, after exiting the container which has the porous cell growth support, back to the container which has the porous cell growth support.

For clinical use, a fully-automated gene transfer system is envisioned having the reproducibility and documentation required by the United States Food and Drug Administration. The system would allow automated deposition of particles on cell growth supports, target cell contact, transfected target cell purification and target cell harvesting as needed for gene therapy applications.

The following examples are intended to more-clearly illustrate aspects of the invention, but are not intended to limit the scope thereof.

EXAMPLE I

Contact between particles and target cells is necessary for gene transfer to take place. Particles suspended in a liquid move by random motion, called Brownian motion. A typical prior art transfection method is to overlay attached target cells with a liquid containing particles. In this method, particle-target cell contact is fundamentally limited by Brownian motion, a measure of which is diffusivity. Moreover, even if the liquid is gently agitated, contact remains limited by Brownian motion because of laminar flow. The transfection efficiency in these methods is expected to be directly proportional to the concentration of particles in suspension, the concentration of target cells, and increase with the duration of time that the target cells are exposed to transfection particles.

Figure 2B:
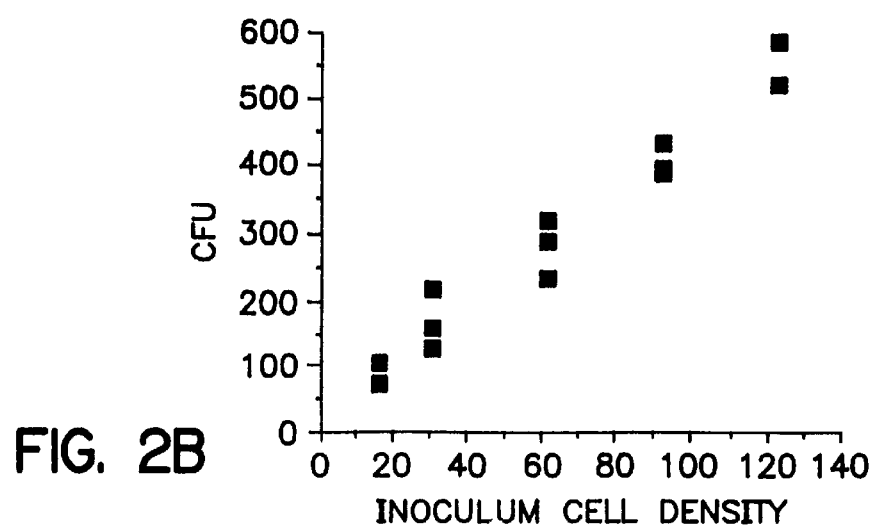

These expectations are verified experimentally. For the results of FIG. 2, African green monkey-derived CV-1 cell line (ATCC# CCL 70) is transfected by a murine retroviral particles produced by a ψCRIP derived producer cell line carrying the LacZ gene for β-galactosidase. FIG. 2a shows that for a fixed number of target cells and transfection time, the transfection efficiency is directly proportional to the concentration of viral particles. Similarly, FIG. 2b shows that for a given viral particle concentration and transfection time, the transfection efficiency is directly proportional to the density of target cells.

Particles lose their ability to transfect target cells over time. The loss occurs for various reasons including, for example, particle disintegration. The half-life measures the time in which half of the particles in a population are lost. In suspension, the net distance that particles can travel is limited by particle diffusivity and half-life. For particles in suspension having a short half-life, particles can only travel a very short distance. This distance is critical for transfection because only particles within it can transfect target cells. The critical distance can be estimated based on fundamental laws that govern Brownian motion as well as be experimentally determined. For retroviral particles, the critical distance is calculated to be about 380 to 440 $\mu$m. The calculation is based on retroviral particles traveling for about one half-life, about 4.5 to 6 hours long, and a diffusion coefficient of about $4.5 \times 10^{-8}$ cm$^2$/sec. After four retroviral half-lives, corresponding to 760 to 880 $\mu$m, approximately 93% of the retroviral particles cannot transfect target cells. For calculations see, for instance, E. L. Cussler, *Diffusion, Mass Transfer in Fluid Systems*, Cambridge University Press, Cambridge (1984).

Figure 2C:
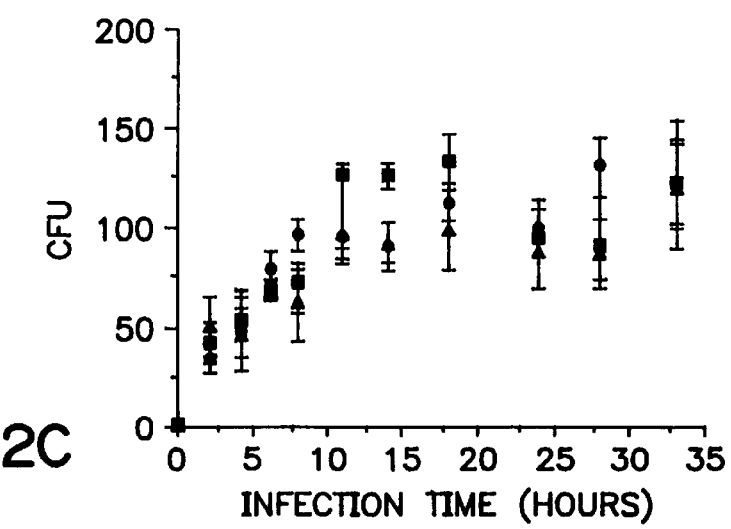

Experimentally, the critical distance that retroviral particles can move by Brownian motion and transfect target cells can be shown to be less than about 500 $\mu$m. In FIG. 2c, three depths of liquid containing equivalent concentrations of retroviral particles are placed on top of adherent target cells for different lengths of time. The three depths of liquid are 520, 832, and 1559 $\mu$m, and are denoted in FIG. 2c by different data point symbols. FIG. 2c shows that all three depths have essentially the same transfection over time, showing two important points. First, transfection does not increase after about 12 to 15 hours or approximately 2 to 3 retroviral half-lives. Second, retroviral particles more than 520 $\mu$m away from the target cells do not significantly transfect cells because greater depths of liquid do not increase transfection. Therefore, the critical distance that retroviral particles can diffuse and transfect target cells approximately 520 $\mu$m or less. Current methods typically use a liquid depth of about 3000 $\mu$m (3 mm) above the target cells for transfection. These methods, thus, waste the vast majority of retroviral particles because the retroviral particles beyond the short critical distance never transfect the target cells.

EXAMPLE II

Figure 3A:
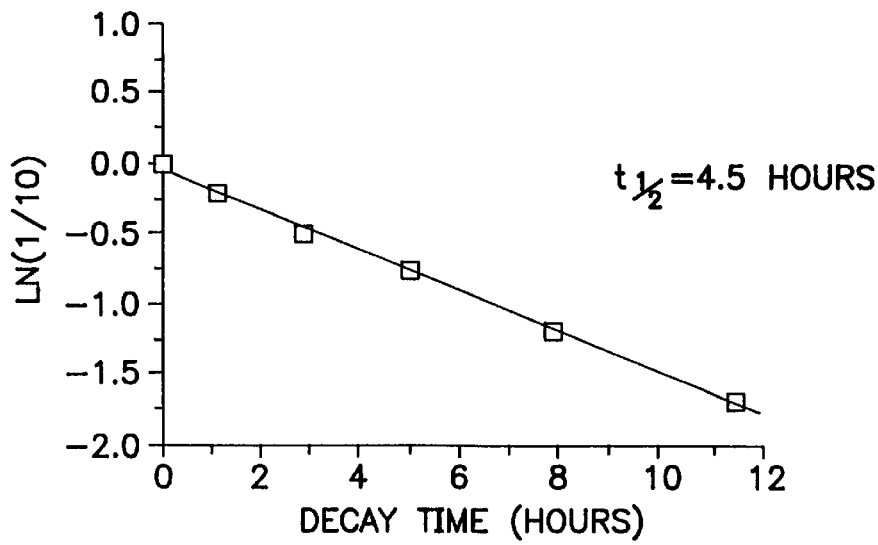
FIGS. 3A–C shows infectivity decays for retroviral particles in: (A) in suspension, (B) on a cell growth support due to stagnant loading, and (C) on a cell growth support due to filtration deposition.
Figure 3B:
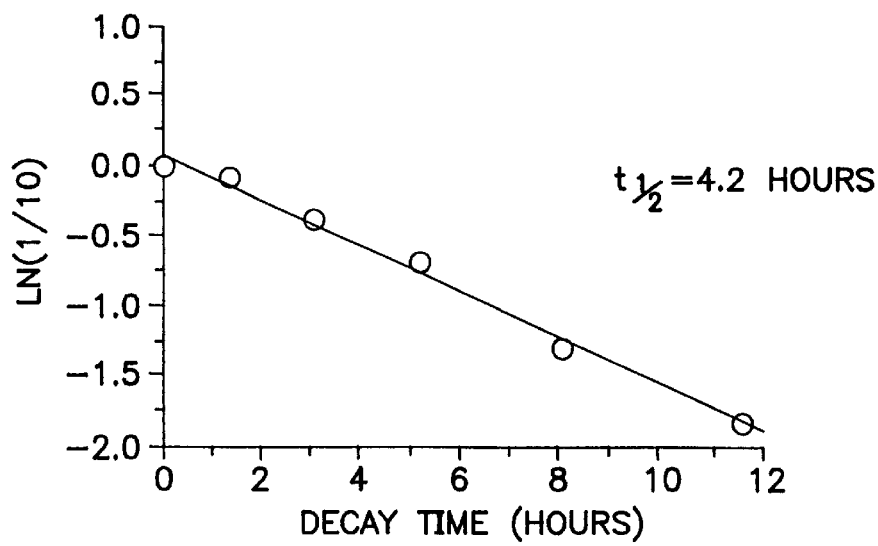
Figure 3C:
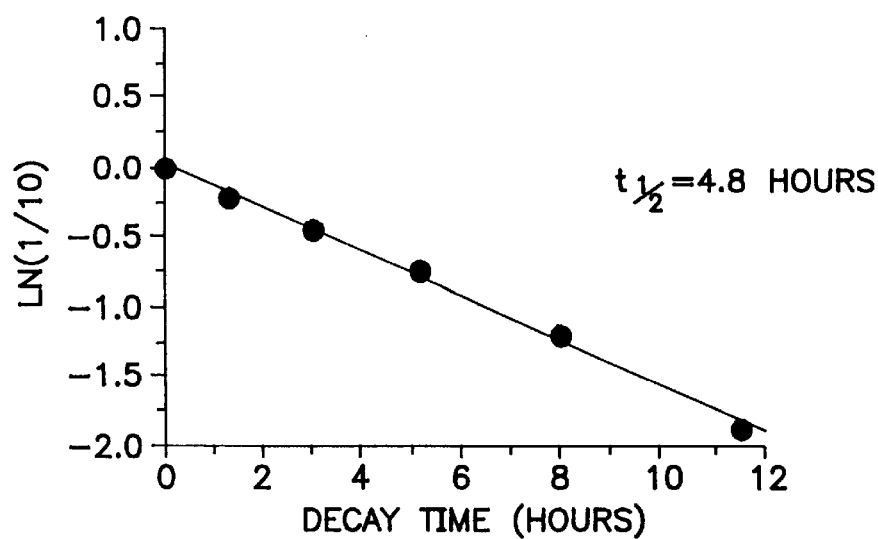
Figure 4:
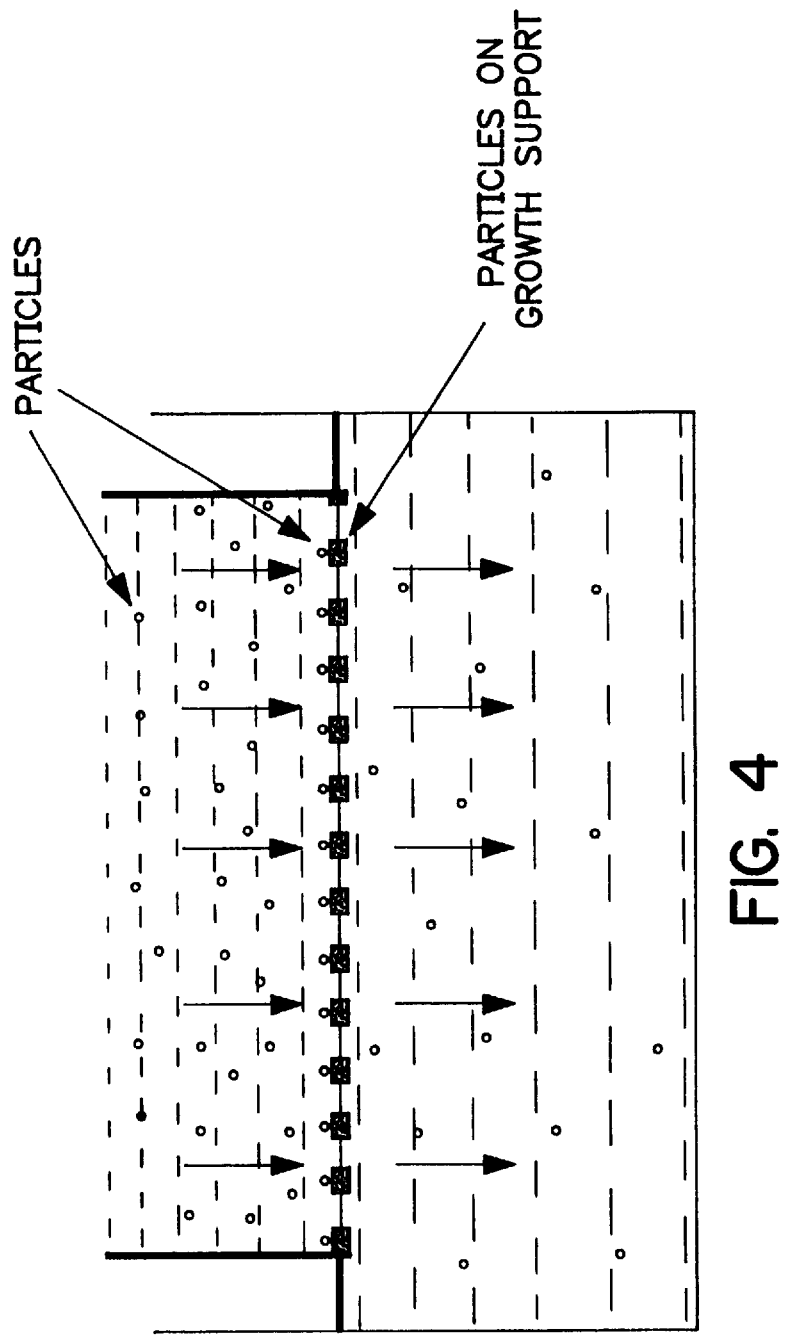
FIG. 4 depicts an embodiment of the invention in which particles are deposited on a cell growth support by flowing the fluid containing the particles through a porous cell growth support.
Figure 5:
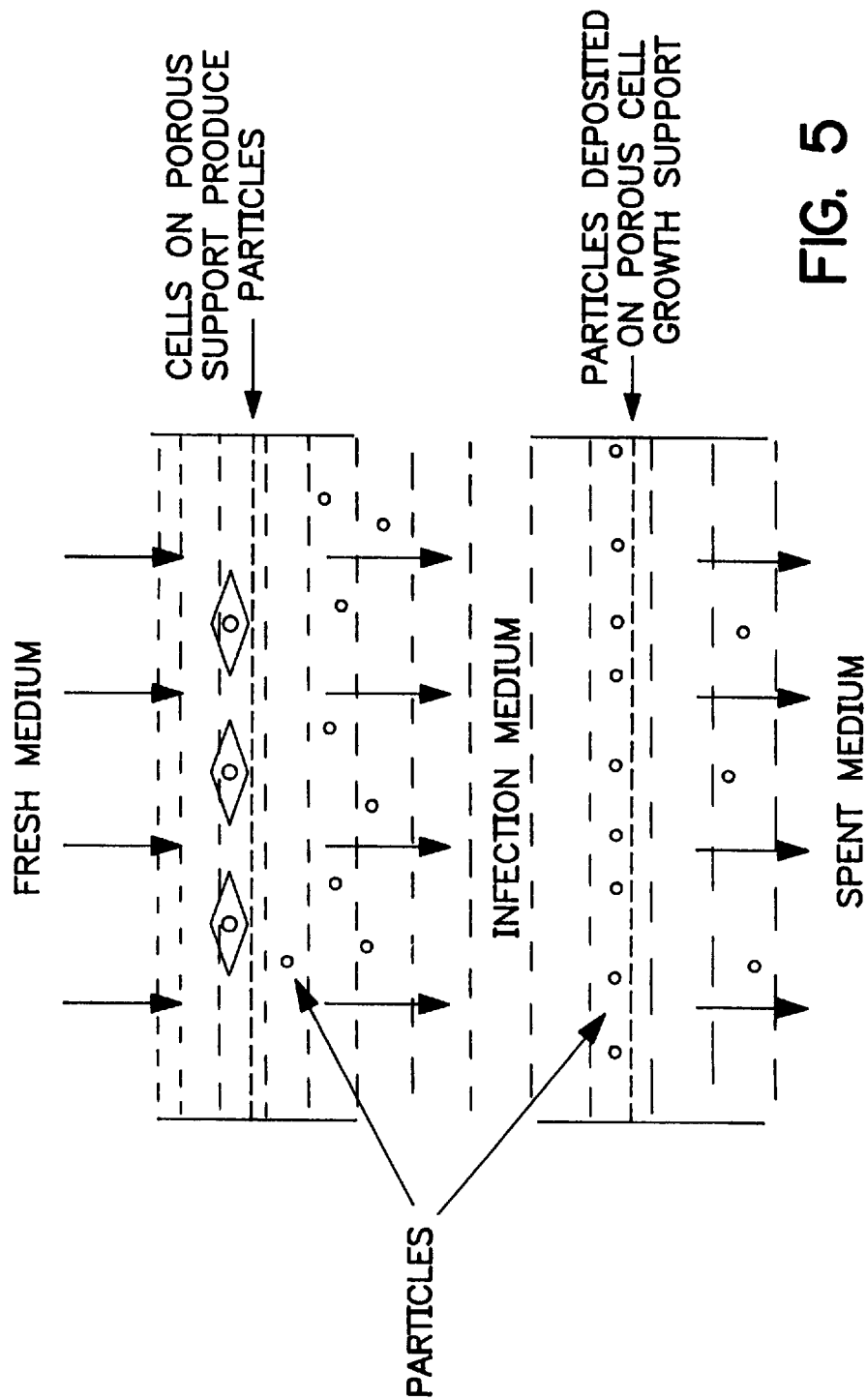
FIG. 5 depicts an embodiment of the invention in which viral particles are deposited on a cell growth support by connecting a chamber producing viral particles to a chamber containing a porous cell growth support.

FIG. 3 shows the decay of retroviral particles: (A) suspended in liquid; (B) on a cell growth surface deposited by adsorption from stagnant liquid; and (C) on a cell growth support deposited by filtration adsorption. The half-lives for the three cases are 4.8, 4.2 and 4.6 hours, respectively.

The viral particles are replication incompetent retroviral particles from a PA317/pMFG packaging cell line and the target cells are NIH 3T3 murine fibroblast cells (ATCC# CRL 1658). Particles are deposited onto porous cell growth supports (COSTAR TRANSWELL insert, 0.4 $\mu$m pore diameter PE filter, cat. no. 3450). Filtration particle deposition is by vacuum filtering the fluid containing the particles through the porous cell growth supports using a water aspirator. Stagnant particle deposition is done by overlaying the porous cell growth support with fluid containing the particles for 2 hours. An equivalent particle fluid volume containing an equivalent number of particles as for the particles in suspension is used to particle-load the porous cell growth supports. An equivalent number of target cells are used in both groups, approximately 30,000 per insert, and allowed to naturally attach to the cell growth supports. The same standard transfection fluid, including 4 $\mu$g/ml polybrene, and conditions are used for transfecting both groups. The target cells are transfected for 24 hours.

The data of FIG. 3 has at least three important ramifications. First, it shows retroviral particle half-life is short and, as discussed above, the short half-life severely limits the distance in which these particles can travel in solution.

Second, FIG. 3 shows retroviral particles deposited on cell growth supports by filtration deposition have the same half life as particles in suspension or deposited on cell growth supports by adsorption from stagnant liquid. The half-life remains the same despite the fact that an increased number of particles are localized on the cell growth support by filtration deposition. Generally, increasing retrovirus concentration significantly reduces the retrovirus half-life. The claimed invention, unlike prior art viral concentration methods, produces the unexpected result that locally concentrating retroviral particles on a cell growth support do not reduce infectivity. See, for example, Mulligan, R. C., "The Basic Science of Gene Therapy," *Science* 260:926–932 (14 May 1993), see especially page 926, last paragraph bridged to page 927.

Third, filtration deposition results in a Peclet number exceeding unity. As a result, the effective amount of particles deposited on the cell growth support by filtration deposition is greater than that from stagnant liquid. Particle-loaded cell growth supports made by filtration deposition and stagnant liquid adsorption have an initial transfection efficiency of 46% and 24%, respectively.

EXAMPLE III

Table 1 shows the transfection efficiencies of particles in suspension and particles deposited on a cell growth support by filtration deposition. Approximately 24% and 54% of the target cells are transfected by the particle-suspension and particle-loaded cell growth support methods, respectively.

The viral particles are replication incompetent retroviral particles from a PA317/pMFG packaging cell line and the target cells are NIH 3T3 murine fibroblast cells (ATCC#

CRL 1658). Particles are deposited onto porous cell growth supports (COSTAR TRANSWELL insert, 0.4 μm pore diameter PE filter, cat. no. 3450) by vacuum filtering the fluid containing the particles using a water aspirator. An equivalent particle fluid volume containing an equivalent number of particles as for the particles in suspension is used to particle-load the porous cell growth support. An equivalent number of target cells are used in both groups, approximately 30,000 per insert, and allowed to naturally attach to the cell growth supports. The same standard transfection fluid, including 4 μg/ml polybrene, and conditions are used for transfecting both groups. The target cells are transfected for 24 hours. Transfection efficiency is the number of transfected cells divided by total target cells times 100.

TABLE 1

| TRANSFECTION METHOD | TRANSFECTION EFFICIENCY (% of TOTAL CELLS) |
|---|---|
| Particles in suspension | |
| Experiment 1 | 23.2 |
| Experiment 2 | 24.5 |
| Average | 23.9 |
| Particle-loaded cell growth support | |
| Experiment 1 | 47.5 |
| Experiment 2 | 59.4 |
| AVERAGE | 53.5 |

EXAMPLE IV

Table 2 shows transfection efficiency and recovery of retroviral particles deposited on a porous cell growth support before and after a freeze/thaw cycle. Approximately 68% of the transfection efficiency is recovered after freeze/thaw.

The retroviral particles are produced by the PA317/pMFG retroviral packaging cell line. The retroviral particles are suspended in standard cell culture fluid to which 4 μg/ml polybrene is added. The porous cell growth support used is a COSTAR TRANSWELL 0.4 μm PE membrane insert (COSTAR cat. no. 3450). The retroviral particles are deposited on the inserts by vacuum deposition using a water aspirator. Particle-loaded cell growth supports are frozen by and stored in a −80° C. freezer (REVCO) and thawed 24 hours later in 37° C. cell culture medium. The recovery is the transfection efficiency after the freeze/thaw cycle divided by the transfection efficiency before the freeze/thaw cycle.

TABLE 2

| EXPERIMENT | TRANSFECTION EFFICIENCY BEFORE FREEZE/THAW (% of TOTAL CELLS) | TRANSFECTION EFFICIENCY AFTER FREEZE/THAW (% of TOTAL CELLS) | % RECOVERY |
|---|---|---|---|
| 1 | 7.8 | 5.1 | 66 |
| 2 | 53.4 | 30.1 | 56 |
| 3 | 24.5 | 19.7 | 81 |
| AVERAGE | | | 68 |

EXAMPLE V

Tables 3 and 4 show the transfection efficiencies of particles in suspension and particles deposited on cell growth supports by filtration deposition with and without the chemical additive, polybrene. The particle-loaded cell growth supports without a chemical additive result in transfection efficiencies as good as or better than that achieved by prior art methods with a chemical additive. This result is unexpected because the claimed invention is the only method that does not require a chemical additive for transfection.

The viral particles are replication incompetent retroviral particles from a PA317/pMFG packaging cell line containing the lacZ gene and the target cells are NIH 3T3 cells. Particles are deposited as in Example III. An equivalent number of target cells are used in all groups and allowed to naturally attach to the cell growth supports. For those groups containing polybrene, 4 μg/ml polybrene is added to the DMEM with 10% FCS transfection liquid used for all groups. The same standard transfection conditions are used for all groups.

The transfection efficiency is assayed by either of two methods, flow cytometry or microscopic counting. For flow cytometry, the FDG stain identifies infected from non-infected target cells and cells analyzed using standard flow cytometer counting methods. For microscopic counting, the X-gal blue stain identifies infected from non-infected target cells and cells analyzed using standard microscopic cell examination and counting methods. The results obtained by flow cytometry and microscopic counting are shown in Tables 3 and 4, respectively. The results are expressed as transfection efficiency.

TABLE 3

| TRANSFECTION LIQUID | PARTICLES IN SUSPENSION (% OF TOTAL CELLS) | PARTICLE-LOADED CELL GROWTH SUPPORT (% OF TOTAL CELLS) |
|---|---|---|
| WITH POLYBRENE | 16.8 | 30.0 |
| WITHOUT POLYBRENE | 1.9 | 19.8 |

TABLE 4

| TRANSFECTION LIQUID | PARTICLES IN SUSPENSION (% OF TOTAL CELLS) | PARTICLE-LOADED CELL GROWTH SUPPORT (% OF TOTAL CELLS) |
|---|---|---|
| WITH POLYBRENE | 23.7 | 41.4 |
| WITHOUT POLYBRENE | 2.4 | 33.7 |

EXAMPLE VI

Figure 6:
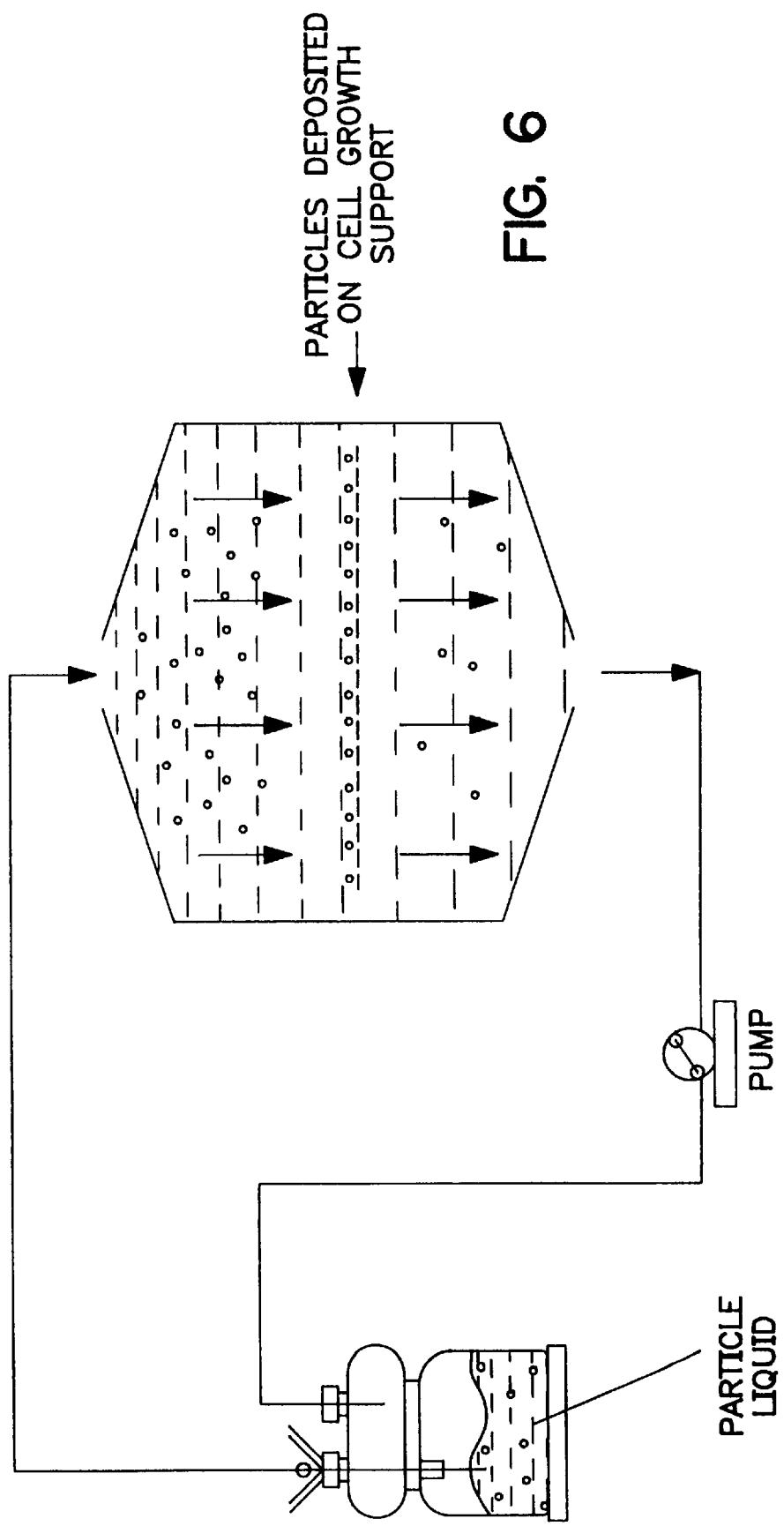
FIG. 6 depicts an embodiment of the invention in which viral particles are deposited on cell growth supports by connecting a container producing viral particles to a chamber containing a porous cell growth support in which medium is recycled by means of a pump.

FIG. 6 is a schematic diagram of an apparatus used to particle load cell growth supports. The apparatus includes a first container in which particles are deposited on a cell growth support. The first container includes a clamp which allows the container to opened and closed for inserting an removing cell growth supports. The container including clamp is made from machinable plastic, glass and metal parts, including, for example polycarbonate, polysufone and stainless steel, which can be sterilized. The clamp forms a hermetic seal when closed which allows liquid to flow through the container. The container dimensions allow the cell growth support to fit within the container. The cell growth support is a pre-sterilized, porous, tissue culture well plate insert available from, for example, COSTAR, MILLIPORE and NUNC. The first container is operationally connected to a pump and a second container containing particles in liquid. The pump is a peristaltic pump which allows sterile liquid pumping. The peristaltic pump is capable of producing sufficient pressure to pump the fluid from the second container and through the insert. The second container can be opened and subsequently hemetrically sealed. The second container can be made of the same materials as the container containing the insert. The second container contains sufficient liquid to particle load the insert. The first and second containers and pump are connected by tubing which can be sterilized, for example, TYGON tubing. The apparatus, first and second containers, pump and tubing, is sterilized prior to use using conventional sterilization methods such as an autoclave and alcohol wipe down. Liquid containing particles and inserts are placed in the apparatus in a way which preserves the sterility of the liquid, inserts and apparatus, such as, for example, in a tissue culture hood using sterile technique.

All articles cited herein are expressly incorporated herein by reference.

I claim:

1. A method of transfecting target cells with particles comprising the steps of:
    a) depositing the particles on a cell growth support in an amount effective for increasing the transfection efficiency of target cells compared to that achieved by particles suspended in liquid; and
    b) contacting the target cells with the particle-loaded cell growth support.

2. The method of claim 1 wherein the particles are viral particles.

3. The method of claim 1, wherein the particles are liposome, spheroplast, red blood cell ghost, DNA-calcium phosphate precipitate or DNA-DEAE Dextran carriers.

4. The method of claim 1 wherein the target cells are animal cells.

5. The method of claim 1 wherein the target cells are hematopoietic stem cells.

6. The method of claim 1 wherein the cell growth support is a filter, membrane filter, cell culture surface, or tissue engineering material.

7. The method of claim 1 wherein depositing the particles on the cell growth support is achieved by filtering or adsorbing the particles onto the cell growth support.

8. The method of claim 1 further comprising the step of removing an inhibitor from the particle-loaded cell growth support prior to contacting the target cells with the particle-loaded cell growth support.

9. The method of claim 1 wherein the particles are replication-incompetent retroviral particles, the target cells are hematopoietic stem cells and the cell growth support is a filter or membrane filter.

10. The method of claim 1 further comprising the step of freezing and/or lyophilizing the particle-loaded cell growth support before contacting the target cells with the particle-loaded cell growth support in a manner which allows the particles to transfect the target cells.

11. The method according to claim 1, wherein the target cells are in vivo.

12. The method according to claim 1, wherein the target cells are in vitro.

13. The method according to claim 1, wherein the target cells are ex vivo.

14. The method of claim 2 wherein the viral particles are RNA viral particles.

15. The method of claim 2 wherein the viral particles are DNA viral particles.

16. The method of claim 4 wherein the animal cells are human cells.

17. The method of claim 6 wherein the cell growth support is a filter or membrane filter.

18. The method of claim 6 wherein the cell growth support is a cell culture surface.

19. The method of claim 6 wherein the cell growth support is a tissue engineering material.

20. The method of claim 7 wherein the cell growth support contains a polycation in an amount effective for attachment of the particles to the cell growth support.

21. The method of claim 14 wherein the RNA viral particles are selected from the group consisting of tobacco mosaic viral particles, cucumber mosaic viral particles, brome mosaic viral particles and retroviral particles.

22. The method of claim 15 wherein the DNA viral particles are selected from the group consisting of SV40 particles, polyoma particles, adenovirus particles, Epstein-Barr particles, vaccinia particles, herpes simplex particles, papilloma particles and baculovirus particles.

23. The method of claim 20 wherein the polycation is polybrene or protamine sulfate.

24. The method of claim 21 wherein the RNA viral particles are retroviral particles.

25. The method of claim 24 wherein the retroviral particles are replication-incompetent retroviral particles.

26. A composition comprising particles which transfect target cells, wherein said particles are localized on a filter, membrane filter, cell culture surface or tissue engineering material in an amount effective for increasing the transfection efficiency of target cells compared to that achieved by particles suspended in liquid.

27. The composition of claim 26 wherein the particles are viral particles.

28. The composition of claim 26, wherein the particles are liposome, spheroplast, red blood cell ghost, DNA-calcium phosphate precipitate or DNA-DEAE Dextran carriers.

29. The composition of claim 26 wherein the filter, membrane filter, cell culture surface or tissue engineering material contains a polycation in an amount effective for attachment of the particles to the cell growth support.

30. The composition of claim 26 wherein the cell growth support is a filter or membrane filter.

31. The composition of claim 26 wherein the cell growth support is a cell culture surface.

32. The composition of claim 26 wherein the cell growth support is the tissue engineering material.

33. The composition of claim 26 further comprising target cells in a liquid in contact with the particles.

34. The composition of claim 26 wherein the particle-loaded cell growth support is frozen or lyophilized.

35. The composition of claim 27 wherein the viral particles are RNA viral particles.

36. The composition of claim 27 wherein the viral particles are DNA viral particles.

37. The composition of claim 29 wherein the polycation is polybrene or protamine sulfate.

38. The composition of claim 35 wherein the RNA viral particles are selected from the group consisting of tobacco mosaic viral particles, cucumber mosaic viral particles, brome mosaic viral particles and retroviral particles.

39. The composition of claim 35 wherein the RNA viral particles are retroviral particles.

40. The composition of claim 36 wherein the DNA viral particles are selected from the group consisting of SV40 particles, polyoma particles, adenovirus particles, Epstein-Barr particles, vaccinia particles, herpes simplex particles, papilloma particles and baculovirus particles.

41. The composition of claim 39 wherein the retroviral particles are replication-incompetent retroviral particles.

* * * * *

UNITED STATES PATENT AND TRADEMARK OFFICE
CERTIFICATE OF CORRECTION

PATENT NO. : 5,811,274
DATED : Sep. 22, 1998
INVENTOR(S) : Bernhard Ø Palsson

It is certified that error appears in the above-identified patent and that said Letters Patent is hereby corrected as shown below:

In column 6, line 50, please delete "eny" and replace therefor with --env--.

Signed and Sealed this

Twenty-ninth Day of May, 2001

*Attest:*

NICHOLAS P. GODICI

*Attesting Officer*     *Acting Director of the United States Patent and Trademark Office*